United States Patent
Bortz

(10) Patent No.: US 10,912,796 B2
(45) Date of Patent: Feb. 9, 2021

(54) PHOSPHORUS-SPARING NUTRITIONAL COMPOSITION

(71) Applicant: Albion Laboratories, Inc., Layton, UT (US)

(72) Inventor: Jonathan David Bortz, St. Louis, MO (US)

(73) Assignee: Albion Laboratories, Inc., Layton, UT (US)

( * ) Notice: Subject to any disclaimer, the term of this patent is extended or adjusted under 35 U.S.C. 154(b) by 291 days.

(21) Appl. No.: 14/772,558

(22) PCT Filed: Mar. 13, 2014

(86) PCT No.: PCT/US2014/025403
§ 371 (c)(1),
(2) Date: Sep. 3, 2015

(87) PCT Pub. No.: WO2014/159886
PCT Pub. Date: Oct. 2, 2014

(65) Prior Publication Data
US 2016/0015746 A1    Jan. 21, 2016

Related U.S. Application Data

(60) Provisional application No. 61/785,062, filed on Mar. 14, 2013.

(51) Int. Cl.
| | |
|---|---|
| *A61K 33/42* | (2006.01) |
| *A23L 33/165* | (2016.01) |
| *A23L 29/00* | (2016.01) |
| *A23L 33/16* | (2016.01) |
| *A61K 31/194* | (2006.01) |
| *A61K 38/46* | (2006.01) |

(52) U.S. Cl.
CPC ............ *A61K 33/42* (2013.01); *A23L 29/06* (2016.08); *A23L 33/16* (2016.08); *A23L 33/165* (2016.08); *A61K 31/194* (2013.01); *A61K 38/465* (2013.01); *A23V 2002/00* (2013.01); *A23V 2200/306* (2013.01); *A23V 2250/1578* (2013.01); *C12Y 301/00* (2013.01)

(58) Field of Classification Search
CPC .... A61K 33/42; A61K 31/194; A61K 38/465; A23L 33/16; A23L 33/165; A23L 29/06; A23V 2002/00; A23V 2250/1578; A23V 2200/306; C12Y 301/00
IPC ................ A23V 2002/00,2200/306, 2250/1578
See application file for complete search history.

(56) References Cited

U.S. PATENT DOCUMENTS

| | | |
|---|---|---|
| 2005/0037089 A1 | 2/2005 | Jobbins |
| 2008/0081088 A1 | 4/2008 | Lederman et al. |
| 2008/0193531 A1* | 8/2008 | Hermelin ............ A61K 9/2013 424/474 |
| 2009/0068190 A1* | 3/2009 | Bortz ................... A61K 31/10 424/141.1 |
| 2010/0330163 A1 | 6/2010 | Soparkar |
| 2011/0171187 A1 | 7/2011 | Moore et al. |
| 2012/0107296 A1 | 5/2012 | Isaksen et al. |

FOREIGN PATENT DOCUMENTS

WO     2002/098442 A2    12/2002

OTHER PUBLICATIONS

Sharma et al., J. Food Prot. 64: 2053-2057 (2001).*
Wikipedia, https://web.archive.org/web/20120223234615/https://en.wikipedia.org/wiki/Genistein, archived Feb. 23, 2012, accessed Jul. 31, 2017.*
DiSilvestro et al., FASEB J. 22 (meeting abstract supplement): 693.3 (2008).*
Wikipedia, https://web.archive.org/web/20110213080853/https://en.wikipedia.org/wiki/Cholecalciferol, archived Feb. 13, 2011, accessed Jul. 31, 2017.*
NIH, https://ods.od.nih.gov/factsheets/VitaminK-HealthProfessional/, accessed Jul. 31, 2017.*
Hallberg et al., "Iron absorption in man: ascorbic acid and dose-dependent inhibition by phytate," Am. J. Clin. Nutr., 1989, pp. 140-144, vol. 49, No. 1.
Heaney, et al., "Calcium effects on phosphorus absorption: implications for the prevention and co-therapy of osteoporosis," J. Am. Coll. Nutr., 2002, pp. 239-244, vol. 21, No. 3.
Sandberg, et al., "Dietary Aspergillus niger phytase increases iron absorption in humans," J. Nutr., 1996, pp. 476-480, vol. 126, No. 2.
Troesch, et al., "Optimization of a phytase-containing micronutrient powder with low amounts of highly bioavailable iron for in-home fortification of complementary foods," Am. J. Clin. Nutr., 2009, pp. 539-544, vol. 89, No. 2.
International Search Report for PCT Application No. PCT/US2014/25403, 1 page.
Office Action for MX/a/2015/012464 dated Apr. 10, 2019; 5 pages.

* cited by examiner

*Primary Examiner* — Aradhana Sasan
*Assistant Examiner* — Quanglong N Truong

(57) ABSTRACT

A nutritional composition comprises (a) one to a plurality of physiologically acceptable calcium salts and/or chelates and (b) one or more phosphorus-containing components, such as phosphate salts, and/or phosphorus-rescuing components, such as phytase. The composition is useful for phosphorus-sparing calcium supplementation of the diet of a human subject, and for treatment of a low bone density condition in a human subject in need thereof.

21 Claims, No Drawings

PHOSPHORUS-SPARING NUTRITIONAL COMPOSITION

CROSS REFERENCE TO RELATED APPLICATIONS

This application claims the priority of PCT Application PCT/US2014/025403, filed Mar. 13, 2014, which claims the benefit of U.S. provisional application No. 61/785,062, filed Mar. 14, 2013, each of which is hereby incorporated by reference in its entirety.

FIELD OF THE INVENTION

The present invention relates to nutritional compositions useful in providing supplementary calcium to a human subject in need thereof, more particularly to a human subject having a condition characterized by low bone density or at elevated risk of such a condition. The invention further relates to methods of nutritional supplementation to such a subject comprising orally administering a composition of the invention. The invention still further relates to methods for treating a low bone density condition such as osteopenia or osteoporosis in a subject in need thereof, comprising orally administering a composition of the invention.

BACKGROUND OF THE INVENTION

Calcium and phosphorus are essential mineral nutrients for the human body. Individually they serve a variety of important functions; together they provide mineral density, strength and hardness to bone. Recommended dietary intakes of calcium and phosphorus are from 700 to 1300 mg per day and 500 to 1250 mg per day respectively, depending on age (Institute of Medicine: Dietary Reference Intakes for Calcium and Vitamin D, updated November 2010; Dietary Reference Intakes for Calcium, Phosphorus, Magnesium, Vitamin D and Fluoride, 1997). Dairy products and green vegetables are important dietary sources of calcium, while meat and dairy products are important sources of phosphorus. Cereals and cereal products also contain substantial levels of phosphorus, but a large proportion of this phosphorus is locked up in phytates which are not readily digested in the human gastrointestinal (GI) tract, rendering their phosphorus largely unavailable.

Deficiency of either calcium or phosphorus or both can lead to reduced bone mineralization, manifesting as low bone density. The term "bone density" herein refers to bone mineral density (BMD), a measure of the amount of mineral matter in bone as determined, for example, by dual energy x-ray absorptiometry or by ultrasound. It is often reported as a statistical parameter known as a t-score, which is the number of standard deviations above or below the mean for a healthy 30-year-old adult of the same sex and ethnicity as the subject. A t-score of −1.0 to −2.5 is defined as osteopenia, and a t-score below −2.5 as osteoporosis.

Bone tissue is continually being broken down (bone resorption) and built up (bone formation) throughout life; the combined effect of these processes is known as bone remodeling. Where bone resorption becomes excessive, an increased supply of calcium and phosphorus is needed to promote bone formation and restore the balance. For individuals obtaining sufficient calcium from dietary sources, phosphorus nutrition is generally not an issue, as most calcium-rich foods also contain adequate phosphorus in bioavailable form. However, the high doses of supplemental calcium recommended for individuals having, or at risk of, low bone density, particularly osteoporosis, can throw the relative intake of calcium and phosphorus out of balance. An increased calcium-to-phosphorus (Ca:P) ratio can compromise osteoblastic (bone formative) activity, and furthermore can increase osteoclastic (bone resorptive) activity, limiting the benefits of calcium supplementation. The increase in Ca:P ratio resulting from calcium supplementation is further exacerbated by a tendency of calcium to reduce availability of phosphorus from dietary sources, particularly where the diet is rich in phytates. Indeed, Heaney & Nordin (2002) *J. Am. Coll. Nutr.* 21(3), 239-244 have estimated that for every 500 mg elemental calcium equivalent ingested, phosphorus absorption is decreased by 166 mg.

An explanation for this effect is found in the properties of phytates. In foods of plant origin, a high proportion of phosphate groups (overwhelmingly the major source of phosphorus in human nutrition) is bound with the carbohydrate myo-inositol to form a tri- to hexaphosphate ester known as phytic acid or phytate. In the hexaphosphate (IP6) form:

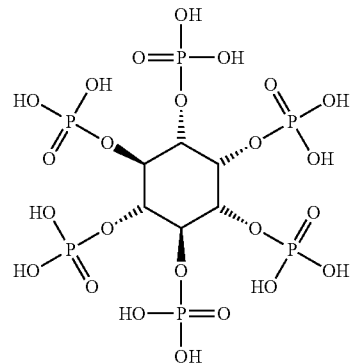

phosphate groups account for 86% of the molecular mass (660) of phytate. Cereal- or legume-rich human diets in the developed world can provide a daily phytate intake up to about 1 g; for vegetarians the daily phytate intake can be as high as 2-2.6 g. Phytate not only locks up phosphorus, reducing its availability for absorption in the human gastrointestinal tract, but it forms stable complexes with positively-charged food components including mineral nutrient cations such as calcium, iron and zinc, reducing their bioavailability too. Complexation of phytate with calcium ($Ca^{2+}$) ions further reduces phosphate release from the phytate by activity of hydrolase enzymes in the gastrointestinal tract; this appears to explain, at least in part, the negative impact of calcium supplementation on phosphorus absorption from dietary sources as noted by Heaney & Nordin (2002), above. Penta-, tetra- and triphosphate forms of phytate (IP5, IP4 and IP3 respectively) have progressively lower binding activity with mineral cations, but nonetheless still bind and inhibit phosphate release, though to a lesser degree than the IP6 form.

Phytate is hydrolysed by enzymes known as phytases, the two main classes of which are 6-phytase, which acts first to free phosphate from the 6-position of the myo-inositol ring, and 3-phytase, which initiates removal of phosphate groups at the 1- and 3-positions. Phytases of plant origin are typically, though not exclusively, 6-phytases, while those produced by micro-organisms (bacteria and fungi including yeasts) are typically 3-phytases. Phytases have not been identified in animal tissues.

Activity of 6-phytases is strongly influenced by pH. For example, 6-phytase from wheat shows an optimum pH for hydrolytic activity of 5.15 and is substantially inactivated at a pH of 2-3. For this reason, 6-phytases tend to be inactive in the acid conditions of the stomach, though (if they are not denatured or degraded during the digestive process) they can provide activity in the more neutral environment of the small intestine. By contrast, microbial 3-phytases are typically active over a wider range of pH. Sandberg et al. (1996) *J. Nutr.* 126(2), 476-480 reported that a recombinant *Aspergillus niger* phytase showed two pH optima: one at pH 2.0 and one at pH 6.0, and was active over a pH range from about 1.0 to about 7.5.

Phytase amounts can be measured by weight (e.g., in mg), but are more usefully expressed in "phytase units", conventionally abbreviated as FTU. By definition, and as understood herein, one FTU is the amount of phytase enzyme that liberates 1 µmol phosphorus per minute from 5.1 mM sodium phytate in pH 5.5 buffer at 37° C.

Hallberg et al. (1989) *Am. J. Clin. Nutr.* 49(1), 140-144 found that ascorbic acid (vitamin C) markedly improved iron absorption from a phytate-rich diet.

Troesch et al. (2009) *Am. J. Clin. Nutr.* 89, 539-544 studied iron absorption from a micronutrient powder used to fortify a phytate-rich meal, maize porridge, consumed by healthy young women. Various combinations of additives were tested for their ability to enhance iron absorption. Recombinant *A. niger* phytase, 10 mg (190 FTU), increased iron absorption by a factor of 1.23 when the iron was given as NaFeEDTA and by a factor of 1.71 when the iron was given as $FeSO_4$. Ascorbic acid alone had little effect on iron absorption from NaFeEDTA, but when ascorbic acid was present the beneficial effect of phytase was apparently more pronounced. In all meals that included phytase, tricalcium phosphate in an amount equivalent to 200 mg elemental calcium was also included. No measurement of phosphorus absorption was recorded.

International Patent Application No. WO 2002/098442 contemplates a dietary supplement or pharmaceutical composition comprising phytase, and its use for increasing the bioavailability of mineral ions such as calcium, magnesium, zinc and iron and for increasing the bioavailability of phosphorus in the form of phosphates. The amount of phytase to be included is not narrowly defined, but can be from 0.1 µg to 250 mg, more especially from 1 µg to 250 mg, preferably from 10 µg to 150 mg (p. 5, lines 19-20).

The product leaflet for OsteoChoice® tablets of Winthrop Pharmaceuticals (Pty) Ltd, South Africa (2008) discloses that each tablet contains, inter alia, 600 mg elemental calcium equivalent (particular calcium salt or salts used not disclosed) and 15 mg (22.5 FTU) phytase. The tablets are said to be "intended as a supplement to add to the nutrients obtained in the diet". It is claimed that the product "may help . . . prevent age-related bone mass loss".

Documents cited above are incorporated herein by reference in their entirety.

Nutritional supplement manufacturers and official dietary recommendations have so far inadequately addressed the need to balance calcium absorption with phosphorus absorption in efforts to retard or reverse progression of low bone density conditions such as osteoporosis, for example in postmenopausal women. This deficiency in the art is corrected by the invention described hereinbelow.

SUMMARY OF THE INVENTION

According to one aspect of the present invention, it is desired to provide a nutritional supplement that, when administered to a human subject, results in absorption of calcium (Ca) and phosphorus (P) in a molar ratio matched as closely as possible to the ratio of these elements utilized in bone remodeling, i.e., a Ca:P molar ratio of about 1.6:1. It will be recognized that, in view of normal biological variation among subjects, relative absorption of Ca and P is best defined as a target rather than a precise outcome. In one embodiment, therefore, the Ca:P molar ratio provided by administration of a particular composition is a calculated ratio based on parameters more fully described below. For example, there is provided a composition, illustratively useful by oral administration for retarding or reversing progression of a low bone density condition in a human subject in need thereof, comprising (a) one to a plurality of physiologically acceptable calcium salts and/or chelates, at least about 5% of the molar amount of calcium in the composition being in the form of one or more organic acid salts and/or chelates of calcium, and (b) one or more phosphorus-containing and/or phosphorus-rescuing components, wherein the total molar amount of phosphorus delivered by such phosphorus-containing component(s) and rescued by such phosphorus-rescuing component(s) is calculated to be about 33% to about 300% of the molar amount of calcium in the composition.

In a related embodiment there is provided a composition, illustratively useful by oral administration for retarding or reversing progression of a low bone density condition in a human subject in need thereof, comprising:

(a) one to a plurality of calcium salts and/or chelates independently selected from the group consisting of calcium carbonate, monocalcium phosphate (MCP), dicalcium phosphate (DCP), hydroxyapatite, calcium citrate tetrahydrate, calcium citrate malate (CCM), calcium formate, calcium gluconate, calcium glycerophosphate, calcium bisglycinate, calcium lactate, calcium levulinate, dicalcium malate (DCM), calcium succinate and calcium tartrate; and (b) one or more phosphorus-containing and/or phosphorus-rescuing components, wherein the total molar amount of phosphorus delivered by such phosphorus-containing component(s) and rescued by such phosphorus-rescuing component(s) is calculated to be about 33% to about 300% of the molar amount of calcium in the composition.

It will be noted that, at an exemplary or target Ca:P molar ratio of 1.6:1, the total molar amount of phosphorus delivered and/or rescued is 62.5% of the molar amount of calcium. A molar amount of phosphorus that is 33% or 300% of the molar amount of calcium represents a Ca:P molar ratio of 3:1 or 1:3 respectively. In practice a large molar excess of phosphorus over calcium, for example as high as 300%, may be unnecessary; in most cases the molar amount of phosphorus delivered and/or rescued will be not more than about 167% of the molar amount of calcium in the composition. Where a composition is described herein as comprising a calcium component (a) and a phosphorus component (b), it will be understood that where a phosphate salt of calcium is present, its calcium is included in component (a) and its phosphorus in component (b).

In another embodiment there is provided a composition, illustratively useful by oral administration for retarding or reversing progression of a low bone density condition in a human subject in need thereof, comprising (a) one to a plurality of physiologically acceptable calcium salts and/or chelates in a total amount equivalent to about 75 to about 750 mg elemental calcium per unit dose, at least about 5% of the molar amount of calcium in the composition being in the form of one or more organic acid salts and/or chelates of calcium; and (b) at least one phytase in a total amount of about 0.1 to about 10 FTU (phytase units) per mg elemental calcium equivalent.

In a still further embodiment there is provided a composition, illustratively useful by oral administration for retarding or reversing progression of a low bone density condition in a human subject in need thereof, comprising (a) at least one physiologically acceptable calcium salt and/or chelate in a total amount equivalent to about 250 to about 750 mg elemental calcium per unit dose; and (b) at least one phytase in a total amount of about 0.1 to about 10 FTU per mg elemental calcium equivalent.

A composition of the invention is useful in a method for supplementing mineral nutrition in a human subject. Thus in a still further embodiment there is provided such a method, comprising orally administering daily to the subject one to a plurality of unit doses of a composition as described herein.

In a still further embodiment there is provided a method for treating a low bone density condition in a human subject in need thereof, for example retarding or reversing progression of such a condition, comprising orally administering daily to the subject one to a plurality of unit doses of a composition as described herein.

Other embodiments, variants thereof and modes of practicing the invention will be evident from the more detailed description that follows.

DETAILED DESCRIPTION

Composition

In one embodiment, a composition comprises (a) one to a plurality of physiologically acceptable calcium salts and/or chelates, at least about 5% of the molar amount of calcium in the composition being in the form of one or more organic acid salts and/or chelates of calcium, and (b) one or more phosphorus-containing and/or phosphorus-rescuing components, wherein the total molar amount of phosphorus delivered by such phosphorus-containing component(s) and rescued by such phosphorus-rescuing component(s) is calculated to be about 33% to about 300% of the molar amount of calcium in the composition.

In another embodiment, a composition comprises (a) one to a plurality of calcium salts and/or chelates independently selected from the group consisting of calcium carbonate, monocalcium phosphate (MCP), dicalcium phosphate (DCP), hydroxyapatite (including microcrystalline hydroxyapatite), calcium citrate tetrahydrate, calcium citrate malate (CCM), calcium formate, calcium gluconate, calcium glycerophosphate, calcium bisglycinate (including calcium glycinate chelate, buffered calcium glycinate chelate and taste-free calcium glycinate chelate), calcium lactate, calcium levulinate, dicalcium malate (DCM; for example Dimacal™ of Albion Laboratories, Inc. and products technically equivalent thereto), calcium succinate and calcium tartrate; and (b) one or more phosphorus-containing and/or phosphorus-rescuing components, wherein the total molar amount of phosphorus delivered by such phosphorus-containing component(s) and rescued by such phosphorus-rescuing component(s) is calculated to be about 33% to about 300% of the molar amount of calcium in the composition.

The compositions described herein contain one or more phosphorus-containing (e.g., phosphate-containing) and/or phosphorus-rescuing (e.g., phosphate-rescuing) components. Phosphorus-containing components include phosphate salts, for example calcium phosphates such as MCP, DCP and TCP, and non-calcium phosphates such as sodium, potassium and magnesium phosphates. Organic sources of available phosphorus such as phosphate esters, e.g., vitamin C phosphate, can also be used. Phosphorus-rescuing components include phosphohydrolases, more particularly phytases as described herein that are capable of liberating phosphorus in biologically available form from phytates in the diet. Optionally the composition further comprises one or more agents that can reduce the calcium-binding effect of phytases, including without limitation ascorbic acid and salts and chelates of minerals such as iron, zinc and magnesium.

The effective Ca:P molar ratio (i.e., supplemental calcium divided by the total of supplemental and rescued P) is about 1:3 to about 3:1, for example about 0.6:1 to about 3:1, or about 1:1 to about 2:1. Expressed as molar amount of P supplied and/or rescued as a percentage of molar amount of Ca, these ranges equate to about 33% to about 300%, for example about 33% to about 167%, or about 50% to about 100%. In a particular embodiment, the molar amount of P supplied and/or rescued is not greater than 65%, for example about 50% to 65%, of the molar amount of Ca.

For present purposes, the effective Ca:P molar ratio is defined as a calculated, not a measured, amount. A formula for calculating the effective Ca:P molar ratio is presented below; from this formula an algorithm can be derived for selecting amounts of phosphate and/or phytase to be included in the composition in order to reach a desired effective Ca:P molar ratio, for example a ratio of about 1.6:1, the ratio utilized in bone remodeling.

A. mmol Ca: calculated as total weight (mg) of elemental Ca equivalent supplied as Ca salt(s) and/or chelate(s)/atomic weight of Ca (approximately 40).

B. mmol P: calculated as the sum of
(1) total weight (mg) of elemental P equivalent supplied as phosphate salt(s)/atomic weight of P (approximately 31); and
(2) if phytase is included in the composition, mmol P rescued from phytate by phytase activity: FTU×0.03 (this assumes activity of phytase in the stomach is 50% of its optimum activity and residence time in the stomach is 1 hour; it also assumes the amount of phytate in the diet is not limiting).

Ca:P ratio: calculated as A/B.

According to the above embodiments, the amount of calcium per unit dose, whether expressed as elemental Ca equivalent or as Ca salt, is not narrowly limiting. A single solid dosage form, such as a tablet or capsule, can conveniently contain up to about 800 mg or more (for example about 250 mg to about 800 mg, about 250 mg to about 750 mg, or about 250 mg to about 550 mg) in total of one or more calcium salts and/or chelates, with or without the presence of phytase. Likewise, the amount of phosphorus supplied is not narrowly limiting, as long as the Ca:P molar ratio as defined above is within the stated range. For example, a single solid dosage form can conveniently contain up to about 800 mg or more (for example about 250 mg to about 800 mg, about 250 mg to about 750 mg, or about 250 mg to about 550 mg) in total of one or more phosphate salts and/or esters, with or without the presence of phytase.

Accordingly, in a further embodiment of the invention there is provided a composition comprising one to a plurality of dose units, each dose unit comprising (a) about 250 mg to about 800 mg in total of one or more calcium salts and/or chelates and (b) a phosphorus-containing component that is separate from or partly or wholly provided by said one or more calcium salts and/or chelates; wherein the molar ratio of calcium to phosphorus delivered by each dose unit is about 1:3 to about 3:1.

In some embodiments of the invention, a composition comprises phytase, as indicated above. In one aspect, such a composition comprises (a) one to a plurality of physiologically acceptable calcium salts and/or chelates in a total amount equivalent to about 75 to about 750 mg elemental calcium per unit dose, at least about 5% of the molar amount of calcium in the composition being in the form of one or more organic acid salts and/or chelates of calcium, and (b) at least one phytase in a total amount of about 0.1 to about 10 FTU per mg elemental calcium equivalent. In another aspect, such a composition comprises (a) at least one physiologically acceptable calcium salt and/or chelate in a total amount equivalent to about 250 to about 750 mg elemental calcium per unit dose, and (b) at least one phytase in a total amount of about 0.1 to about 10 FTU per mg elemental calcium equivalent.

A composition of the invention may be described herein as a "nutritional supplement composition", meaning a composition that comprises at least one nutrient, for example mineral nutrient, essential for human nutrition. The nutrient can be one that is deficient or suboptimal in a particular subject's diet in the amount available for absorption in the subject's GI tract such that the health of the subject can be improved by administration of the composition; or the subject can be at risk of such deficiency or suboptimality. In the present context the at least one nutrient comprises calcium; other mineral nutrients such as magnesium, iron, zinc and/or phosphorus are optionally present in addition to calcium. The composition can optionally also comprise one or more organic nutrients such as vitamins, for example ascorbic acid (vitamin C), vitamin D (which mediates intestinal absorption of calcium), vitamin $K_1$ (also known as phylloquinone, phytomenadione, or phytonadione), and vitamin $K_2$ (menaquinones). The composition can also comprise various flavonoids, such as isoflavones (e.g. genistein). A composition of the invention is suitable for administration by any route that delivers the composition to the stomach and/or intestine, for example per os or via gastric or enteral tube.

In additional embodiments of the invention, a composition as described herein further comprises protein. Several studies have identified associations between dietary protein intake and bone mineral density, rates of bone loss and fracture incidence. Thus, it can be beneficial to include a protein component in a composition described herein or provided as a separate "add-on" supplement to a composition described herein. For example, a composition comprising protein can be in the form of a powder which can be reconstituted with water or milk. Alternatively, the composition can be prepared as a ready-to-drink beverage. Various sources of protein can be used in a composition described herein. For example, soy protein isolate(s) such as a high concentration protein isolated soy formulation (SUPRO® 783 available from DuPont U.S.A.) and a moderate concentration protein isolated soy formulation (SUPRO® LF IP available from DuPont U.S.A.) can be used individually or in combination. Protein may be present in the composition from about 2.5 g to about 7.5 g, or from about 5 g to about 12.5 g, or from about 10 g to about 17.5 g, or from about 15 g to about 30 g, or from about 25 g to about 50 g.

1. Calcium Component

Calcium is present in a composition of the invention in the form of at least one "physiologically acceptable" salt and/or chelate, i.e., a salt or chelate that is non-toxic in the amount to be orally administered and that is capable of releasing calcium ions for absorption in the GI tract. Examples of physiologically acceptable salts and chelates of calcium include, without limitation, inorganic salts such as the carbonate salt ($CaCO_3$) and phosphate salts including monocalcium phosphate (MCP; $Ca(H_2PO_4)_2$), dicalcium phosphate (DCP; $CaHPO_4$), tricalcium phosphate (TCP; $Ca_3(PO_4)_2$) (including Calci-K™ of Albion Laboratories, Inc. and products technically equivalent thereto, which contain TCP together with potassium citrate), and hydroxyapatite (including microcrystalline hydroxyapatite), and salts and chelates with organic acids such as citrate and/or malate (e.g., calcium citrate, calcium citrate tetrahydrate, dicalcium malate (DCM), and calcium citrate malate (CCM)), formate, gluconate, glycerophosphate, glycinate (e.g., calcium bisglycinate, calcium glycinate chelate, buffered calcium glycinate chelate and taste-free calcium glycinate chelate), lactate, levulinate, succinate and tartrate. Salts of calcium and magnesium, such as calcium magnesium carbonate (dolomite), can also be used if desired. As indicated above, in some embodiments at least one of the salts of calcium present in the composition is an organic acid salt, for example any of the salts with organic acids mentioned above. In an illustrative embodiment the calcium is present as DCM, alone or together with TCP.

It is desirable that at least a portion, for example at least about 5%, of the calcium in the composition be in the form of an organic acid salt or chelate such as DCM because of the relatively high solubility of such salts by comparison with inorganic salts such as calcium carbonate or TCP. More soluble salts tend to provide improved bioavailability of calcium, particularly when administered separately from food. However, a drawback with organic acid salts is that they typically provide less elemental calcium equivalent per mg of salt than is the case with inorganic salts. For example, the elemental calcium content of calcium carbonate is about 40% and that of TCP about 38%, whereas that of DCM is only about 29%. Thus, especially where a relatively high calcium dosage amount is desired (for example about 250 mg or more per dose unit), it will generally be found advantageous to include a portion of the calcium in the form of an inorganic salt such as calcium carbonate or TCP. In various embodiments, at least about 5%, at least about 7%, at least about 10%, at least about 15%, at least about 20%, at least about 25%, at least about 33% or at least about 50% of the calcium in the composition is in the form of one or more organic acid salts or chelates, illustratively DCM.

The term "unit dose" herein means an amount of a nutritional supplement or therapeutic composition suitable for a single administration to a human subject in need thereof. A unit dose can be presented as one or more discrete dosage forms such as tablets, pastilles, lozenges or capsules; alternatively the composition can take the form of a non-discrete liquid, powder or granular formulation from which a unit dose can be measured or metered prior to administration. Discrete dosage forms, particularly tablets, are generally preferred for ease of use and accuracy of dosing.

In certain embodiments, the total amount of elemental calcium equivalent per unit dose is about 75 to about 750 mg. The word "about", when qualifying any amount herein, will be understood to mean±15%, preferably ±10%, more preferably ±5%, of the amount so qualified, unless otherwise indicated. Amounts, for example dosage amounts, of calcium presented herein are expressed as elemental calcium equivalent unless otherwise indicated.

Amounts less than about 75 mg per unit dose are generally inadequate for uses of the composition contemplated herein. Such a low dosage amount of calcium is unlikely on its own to provide meaningful benefit to a human subject; and to reach a beneficial dosage amount an inconveniently large number of dose units, e.g., tablets, would have to be administered daily. In various embodiments, a minimum amount of elemental calcium equivalent per unit dose (e.g., per tablet) is about 100, about 150, about 200, about 250, about 300, about 350, about 400, about 450 or about 500 mg.

Amounts greater than about 750 mg, besides being difficult to formulate as a discrete dosage form such as a tablet at a size convenient for oral administration, are generally wasteful as the body cannot absorb such a large dose of calcium at one time. In various embodiments, a maximum amount of elemental calcium equivalent per unit dose (e.g., per tablet) is about 700, about 650 or about 600 mg.

Where a combination of organic and inorganic salts of calcium (e.g., DCM and TCP) is used, the relative amounts of these is not narrowly critical, though typically it will be found desirable to include at least about 25 mg, e.g., about 25 to about 400 mg, more typically about 50 to about 350 mg, elemental calcium equivalent in the form of one or more organic acid salts. For example, about 10% to 100%, more typically about 20% to 100% or about 30% to 100% of the calcium can be in this form. In a particular embodiment, DCM and TCP are present in an elemental calcium equivalent ratio of about 1:9 to about 9:1.

Where a relatively high dosage amount of calcium is required, for example in a nutritional supplement or therapeutic composition providing about 250 to about 750 mg elemental calcium equivalent per unit dose, it becomes less critical to provide a portion of the calcium in the form of an organic acid salt. Thus, in one embodiment of the invention, a composition is provided comprising (a) at least one physiologically acceptable calcium salt in a total amount equivalent to about 250 to about 750 mg elemental calcium per unit dose, and (b) at least one phytase in an amount of about 0.1 to about 10 FTU per mg elemental calcium equivalent.

According to this embodiment, any physiologically acceptable calcium salt or salts can be used, including those mentioned above. Illustratively, a minimum amount of elemental calcium equivalent per unit dose (e.g., per tablet) according to this embodiment is about 300, about 350, about 400, about 450 or about 500 mg, and a maximum amount of elemental calcium equivalent per unit dose (e.g., per tablet) is about 700, about 650 or about 600 mg.

In another embodiment, a composition is provided comprising (a) at least one physiologically acceptable inorganic calcium salt in a total salt amount of about 150 to about 450 mg per unit dose, and (b) at least one phytase in an amount of about 0.1 to about 10 FTU per mg elemental calcium equivalent. Illustratively, a minimum amount of calcium salt per unit dose (e.g., per tablet) according to this embodiment is about 200 or about 250 mg, and a maximum amount of calcium salt per unit dose (e.g., per tablet) is about 400 or about 350 mg.

2. Phytase Component

A composition of any of the embodiments described herein may comprise, in addition to the calcium, at least one phytase. A phytase is a phosphatase enzyme of plant or microbial origin that catalyzes hydrolysis of phytic acid or phytate to release inorganic phosphate (P), in which form the body absorbs and utilizes phosphorus.

In one embodiment, the at least one phytase exhibits phosphatase activity in the pH range typically occurring in the upper GI tract, more particularly the stomach, i.e., about pH 1 to about pH 3. A composition according to this embodiment of the invention can be expected to release $P_i$ from dietary phytate in the stomach, rendering the $P_i$ available for absorption there or in any more distal region of the GI tract. If the at least one phytase additionally exhibits phosphatase activity at higher pH levels, for example about pH 4 to about pH 6, this can be helpful in permitting continued hydrolysis of phytate in the distal duodenum and beyond, where pH is closer to neutral than in the stomach. Many phytases of plant origin (typically 6-phytases) show inadequate activity in the range of about pH 1 to about pH 3, thus phytases of microbial origin (typically 3-phytases), particularly those exhibiting activity both in the pH 1-3 range and at higher pH, are generally preferred. However, a composition as described above wherein the at least one phytase has activity only at pH levels higher than about 3, for example in the pH 4-6 range, is still embraced by the present invention, since, even if it does not rescue a significant amount of bioavailable $P_i$ from phytate in the stomach, it can nonetheless do so in the distal duodenum and beyond.

For example, a composition can comprise a first phytase, exhibiting activity in a pH range from about 1 to about 3. In a particular embodiment, this first phytase is also active in a pH range from about 4 to about 6; alternatively, a composition further comprises a second phytase exhibiting activity in a pH range from about 4 to about 6. In a further embodiment, a composition can comprise a first phytase, exhibiting activity in a pH range from about 4 to about 6.

The phytase component can be formulated for immediate release or controlled (e.g., delayed) release, or both. For example, an immediate-release phytase can provide activity in the stomach. Alternatively or in addition, a portion of the phytase can be formulated to release in the small intestine (duodenum, jejunum and/or ileum) and/or colon. A phytase formulated for immediate release is preferably one that exhibits activity in the pH 1-3 range, and one formulated for release in the intestine preferably exhibits activity in the pH 4-6 range. In a particular embodiment, a composition comprises a first phytase, exhibiting activity in a pH range from about 1 to about 3 and formulated for immediate release, and a second phytase exhibiting activity in a pH range from about 4 to about 6 and formulated for controlled or delayed release. Any known controlled-release or delayed-release formulation technology can be used.

A phytase useful herein can be harvested from a non-engineered organism or from an organism produced by recombinant technology.

In one embodiment, the at least one phytase is derived from one or more plants such as, without limitation, *Avena sativa* (oat), *Lupinus albus* (white lupin) or *Secale cereale* (rye).

In another embodiment, the at least one phytase is derived from one or more fungi such as, without limitation, *Aspergillus niger*, *A. ficuum*, *A. fumigatus*, *Rhizopus microsporus* (e.g., var. *oligosporus*), *Cryptococcus laurentii*, *Saccharomyces cerevisiae* or *Schwanniomyces capriottii*. In a particular aspect, the at least one phytase is derived from *A. niger*, more particularly recombinant *A. niger*. Phytases derived from *A. niger* are commercially available, and non-limiting examples of such phytases include those sold under the trademarks Allzyme™ (Alltech, U.S.A.), Natuphos™ (BASF, Germany), Nutri-Phytase 5000 (Ultra Bio-Logics, Inc., Canada), and also Deerland Phytase (Deerland Enzymes, U.S.A.).

In yet another embodiment, the phytase is derived from one or more bacteria. Non-limiting examples of suitable bacteria include *Bacillus subtilis, Citrobacter braakii, Escherichia coli, Hahella chejuensis, Obesumbacterium proteus, Serratia plymuthica, Yersinia enterocolitica, Y. intermedia, Y. kristensenii, Y. pestis* and *Y. rohdei*. In a particular aspect, the phytase is derived from *E. coli*.

The role of phytase in a composition of the invention is to rescue phosphate in bioavailable form from dietary phytate, so as to provide an improved Ca:P balance for bone remodeling. Phosphate is seldom per se deficient in a normal diet, but so much of it is often locked up in the form of phytic acid or phytate that the amount absorbed can be inadequate for optimal bone remodeling, particularly in subjects having, or at risk of, a low bone density condition such as postmenopausal or age-related osteopenia or osteoporosis. Current official recommendations for calcium supplementation have hitherto failed to account adequately for the adverse effect of supplemental calcium on phosphate release from dietary phytate; a particular benefit of the present invention is that it diminishes, negates or even reverses this adverse effect.

In the study reported by Heaney & Nordin (2002), above, it was calculated that for each 500 mg (12.5 mmol) supplemental calcium ingested, phosphorus absorption was reduced by 166 mg (5.4 mmol). The solution they proposed was to administer at least some of the calcium in the form of calcium phosphate. This can indeed be helpful.

The present invention contemplates an alternative solution to the calcium/phosphorus conundrum, one that, if desired, can be combined with the Heaney & Nordin approach. By the use of phytase to rescue otherwise unavailable phosphate from the diet, the amount of supplemental phosphate required to maintain a healthy Ca:P balance can be substantially reduced or even eliminated.

How much phytase is needed at a minimum to provide a substantial benefit in this regard? As indicated above, amounts of phytase are most meaningfully expressed in FTU. Assuming, per the definition of FTU given herein, that 1 FTU phytase releases 1 μmol phosphorus per minute (or 60 μmol phosphorus per hour) as $P_i$ from phytate under optimum conditions, that at the pH of the stomach the phytase has 50% of its optimum activity, and that average residence time of a meal in the stomach is 60 minutes, the amount of phosphorus rescued in the stomach from a phytate-rich meal by 1 FTU phytase is 0.03 mmol. Further assuming, per the Heaney & Nordin study, that 75 mg supplemental calcium reduces phosphorus absorption by 0.8 mmol, the amount of phytase needed to rescue this amount can be calculated as 0.8/0.03=27 FTU. Higher doses of calcium will require proportionally higher amounts of phytase to make good the loss of available phosphorus; on the present assumptions a suitable amount of phytase per mg elemental calcium equivalent in the composition is 27/75=0.36 FTU. Making allowance for imprecision in the above assumptions and for inter-subject variation, it is believed that a minimally useful amount of phytase according to the present embodiment is about 0.1 FTU per mg elemental calcium equivalent. By comparison, the phytase content of the above-referenced OsteoChoice® tablet is only 22.5/600=0.0375 FTU per mg elemental calcium equivalent.

In calculating an upper limit for the amount of phytase useful in a composition of the invention, it is noted that a meal classified as "highly inhibitory" contains about 1000 mg phytate, and vegetarian meals can contain substantially higher levels, up to about 2500 mg phytate or even more. Phytate has a molecular mass of 660, and 1 mmol phytate, when fully hydrolyzed, releases 6 mmol phosphorus as $P_i$. Complete hydrolysis of 2500 mg phytate would therefore release 2500×6/660=22.7 mmol phosphorus. If, as calculated above, 1 FTU phytase rescues 0.03 mmol phosphorus from a phytate-rich meal, the amount of phytase needed to rescue 22.7 mmol phosphorus is about 750 FTU. This represents about 1 to about 10 FTU per mg elemental calcium equivalent where the amount of supplemental calcium per dose unit is about 75 to about 750 mg as proposed herein.

Thus the person of ordinary skill in the art reading the present disclosure can select an amount of phytase from about 0.1 to about 10, in most cases from about 0.3 to about 3, for example about 0.5 to about 1 FTU per mg elemental calcium equivalent in the composition. Where a phosphate salt such as TCP is included in the composition, the amount of phytase can, if desired, be in the lower part of the range, for example about 0.1 to about 0.7 FTU per mg elemental calcium equivalent; in the absence of phosphate salt it will often be found desirable to provide a greater amount of phytase, for example about 0.5 to about 3, illustratively about 0.7 to about 2 FTU per mg elemental calcium equivalent.

Phytase sources vary in their specific activity. Generally it will be found preferable to use a phytase of relatively high specific activity, illustratively greater than about 2.5 FTU/mg, for example about 2.5 to about 25 FTU/mg. In particular embodiments, the phytase has a specific activity greater than about 3, greater than about 4, greater than about 5 or greater than about 10 FTU/mg. Several commercial phytases used in animal nutrition have advertised specific activities around 5 FTU/mg. A low specific activity phytase such as that present in OsteoChoice™ tablets referenced above (1.5 FTU/mg) can be used but will generally be found inconvenient or difficult to formulate because of the relatively large mass of enzyme protein required. An example of a particularly suitable phytase is a recombinant *A. niger* phytase having a specific activity of about 15 FTU/mg or greater.

3. Other Components

A composition of the invention can optionally contain additional ingredients. As mentioned above, additional mineral nutrients such as magnesium, iron and zinc in the form of salts and/or chelates of these elements can be present, as can vitamins such as ascorbic acid, vitamin D, vitamin $K_1$ and vitamin $K_2$. Flavonoids, such as isoflavones (e.g. genistein) and protein may also be present.

Illustrative salts and chelates of minerals other than calcium that can optionally be present include dimagnesium malate, magnesium aspartate, magnesium creatine chelate, magnesium glycinate chelate (including buffered magnesium glycinate chelate and taste-free magnesium glycinate chelate), magnesium glycyl glutamine chelate, magnesium lysyl glycinate chelate, iron bisglycinate chelate (e.g., Ferrochel™ of Albion Laboratories, Inc. and products technically equivalent thereto), ferrous asparto glycinate chelate (e.g., Sumalate™ of Albion Laboratories, Inc. and products technically equivalent thereto), ferric glycinate (e.g. Iron Taste-Free™ of Albion Laboratories, Inc.), zinc arginate chelate, zinc bisglycinate chelate (including taste-free zinc bisglycinate chelate), citrated zinc bisglycinate chelate, zinc histinate chelate, chromium nicotinate glycinate chelate, copper glycinate chelate, manganese glycinate chelate, molybdenum glycinate chelate, vanadium nicotinate glycinate chelate and combinations thereof.

The term "vitamin D" herein includes not only cholecalciferol (vitamin $D_3$) but analogs, precursors, provitamins and metabolites thereof having vitamin D activity including without limitation ergocalciferol (vitamin $D_2$), 25-hydroxyergocalciferol, 25-hydroxycholecalciferol (25-OH vitamin D) and 1,25-dihydroxycholecalciferol (1,25-diOH vitamin D). The importance of vitamin D in calcium absorption is very well known and need not be further discussed herein; useful amounts if present in a composition of the invention will generally be about 0.1 to about 10 international unit (IU) vitamin D per mg elemental calcium equivalent.

It is contemplated that ascorbic acid or one or more salts or esters thereof can provide some additional benefit in making bound phosphorus available for absorption in the GI tract. Whether the interaction in this regard between phytase and ascorbic acid is synergistic or merely additive is not of consequence for practice of the present invention, it being sufficient to note that useful amounts of ascorbic acid if present in a composition of the invention will generally be about 100 to about 500, for example about 250 to about 400 mg per dose unit.

If desired, additional agents that can benefit bone health can be included in the composition. Illustrative examples of such agents include genistein and vitamin $K_2$ (menaquinone series, for example menaquinone-7). Genistein can illustratively be present in an amount of about 5 to about 50, for example about 10 to about 40 mg per dose unit. Vitamin $K_2$ can illustratively be present in an amount of about 20 to about 200, for example about 50 to about 150 μg per dose unit. An example of a composition comprising such additional components is a composition administered twice per day (BID) having the following:

Calcium Compounds:
(dicalcium malate+pentacalcium hydroxide triphosphate)—500 mg
Phosphate—70 mg
Genistein aglycone—27 mg
Citrated zinc bisglycinate—20 mg
Trans-menaquinone-7—90 μg
Cholecalciferol—400 IU The composition optionally further comprises one or more excipients, selected for example from those conventionally used in preparing pharmaceutical formulations such as diluents, binding agents, dispersants, wetting agents, lubricants, glidants, etc. Many excipients have two or more functions in a pharmaceutical composition. Characterization herein of a particular excipient as having a certain function, e.g., diluent, binding agent, disintegrant, etc., should not be read as limiting to that function.

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; magnesium carbonate; magnesium oxide; bentonite; kaolin; sodium chloride; and the like.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone), for example povidone K-15, K-30 and K-29/32; polyacrylic acids (carbomers); polymethacrylates; and the like.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like.

Suitable wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; sorbitan esters, for example sorbitan monolaurate, sorbitan monooleate, sorbitan monopalmitate and sorbitan monostearate; tyloxapol; and the like.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates.

Other excipients such as buffering agents, stabilizers, antioxidants, antimicrobials, colorants, flavors and sweeteners are known in the pharmaceutical art and can be used. Tablets can be uncoated or can comprise a core that is coated, for example with a nonfunctional film or a release-modifying or enteric coating. Capsules can have hard or soft shells comprising, for example, gelatin and/or HPMC, optionally together with one or more plasticizers.

A composition of the invention can be prepared by any of the conventional processes of pharmacy well known to those of skill in the art.

4. Illustrative Tablets and Capsules

For illustration only, a representative tablet of the invention, as exemplified hereinbelow, comprises about 345 to about 862 mg DCM (equivalent to about 100 to about 250 mg elemental calcium), zero to about 405 mg TCP (equivalent to zero to about 150 mg elemental calcium) and about 100 to about 200 FTU phytase, together with formulation excipients. Optionally, such tablets further comprise about 250 to about 400 mg ascorbic acid or a salt or ester thereof.

A representative capsule of the invention comprises about 138 to about 276 mg DCM (equivalent to about 40 to about 80 mg elemental calcium), about 197 to about 395 mg TCP (equivalent to about 75 to about 150 mg elemental calcium), and zero to about 150 mg dibasic sodium phosphate, together with formulation excipients. Optionally and illustratively the capsule can further comprise one or more of zinc glycinate chelate (in an amount equivalent to about 2.5 to about 5 mg elemental zinc), cholecalciferol (about 250 to about 500 IU), vitamin $K_2$ (about 60 to about 120 µg) and genistein (about 20 to about 40 mg).

Tablets or capsules as described above can deliver, for example, one fifth to one, more typically one half to one, unit dose per tablet.

Method for Supplementing Mineral Nutrition

The invention provides a method for supplementing mineral nutrition in a human subject, comprising orally administering daily to the subject one to a plurality of unit doses of a composition as described above.

A total daily dose of about 100 to about 1500 mg elemental calcium equivalent will generally be found useful according to the present embodiment. Such a total daily dose can be provided in 1 or more, for example 1 to 10, more typically 1 to 3 unit doses of a composition of the invention. Where 2 or more doses are administered daily, they are preferably administered separately, at different times of the day. For total daily doses greater than about 750 mg elemental calcium equivalent, it will clearly be necessary to administer more than one unit dose of a composition of the invention. It is generally recommended that no more than about 500 mg elemental calcium equivalent should be administered orally at any one time. Thus, in some embodiments, for total daily doses up to about 500 mg, once-daily administration is adequate (though the dose can be split if desired); for total daily doses from about 500 to about 1000 mg per day, twice-daily administration is appropriate; and for total daily doses from about 1000 to about 1500 mg per day, twice to three times daily administration is appropriate.

Illustratively, a minimum total daily dose of about 150, about 200, about 250, about 300, about 350, about 400, about 450 or about 500 mg elemental calcium equivalent can be administered. Illustratively, a maximum daily dose of about 1400, about 1300, about 1200, about 1100 or about 1000 mg elemental calcium equivalent can be administered.

Administration is preferably peroral, to deliver the composition directly to the stomach. It is highly desirable, though not essential, to administer a composition of the invention at mealtimes, so that the phytase can go to work during the residence time of the meal in the stomach. For example, the composition can be taken immediately before, during or immediately after a meal. Some subjects may prefer to add the composition to their meal before eating; for this purpose the composition can be provided, for example, in the form of powder or granules in individual single-dose sachets that can be torn open to sprinkle the contents on food, or as a powder mix to be reconstituted with water or a type of milk to form a shake or shake-like composition. The shake or shake-like composition can also be a meal replacement.

The method of the present embodiment can be used to provide phosphorus-sparing calcium supplementation to any human subject, for example a subject whose diet does not provide the full recommended daily allowance of calcium. For example, a subject having short- to long-term intolerance of dairy products (one of the major sources of calcium in western diets) can benefit from the present method. Recommended daily allowance (RDA) of calcium promulgated by the Dietary Supplements Office of the U.S. National Institutes of Health (NIH) is 700 mg for children of 1-3 years, rising to 1000 mg at ages 4-8 and 1300 mg at ages 9-18; for adult men of age 19-70 and women of age 19-50 the RDA is 1000 mg, and for women of 51+ years and men of 71+ years the RDA is 1200 mg.

The term "phosphorus-sparing" in the present context means that the usual reduction in phosphorus availability caused by calcium supplementation is mitigated or eliminated, for example by inclusion of supplemental phosphorus and/or by rescue of phosphorus from dietary phytate as described above.

The present method is also of particular benefit to those on vegetarian or vegan diets, particularly such diets rich in cereal- and/or legume-based foods. The relatively high levels of phytate in these diets lowers availability of calcium and other minerals, particularly iron, zinc and magnesium, and locks up a large proportion of dietary phosphorus in unavailable form. By supplementing the calcium (and optionally other mineral) intake and, at the same time, supplying additional phosphorus and/or rescuing phosphorus by hydrolysis of phytate, the present method can help ensure RDAs are met.

Therapeutic Method

The invention provides a method for treating a low bone density condition, or for retarding or reversing progression of a low bone density condition, in a human subject in need thereof, comprising orally administering daily to the subject one to a plurality of unit doses of a composition as described above.

The terms "treat", "treating", "treatable" and "treatment" herein include reducing or eliminating symptoms of a low bone density condition. They also include promoting underlying physiological processes such as osteoblastic activity involved in bone formation and repair, and/or inhibiting underlying physiological processes such as osteoclastic activity involved in the breakdown of bone. In particular, these terms include positively affecting bone remodeling in a subject having, or at risk of, osteoporosis or bone loss such that the rate of bone loss is reduced or that bone loss is halted or even reversed.

Low bone density conditions treatable by the present method include those manifested as osteomalacia, osteopenia or osteoporosis. In a particular embodiment, the low bone density condition to be treated is age-related or postmenopausal osteopenia or osteoporosis. For example, the subject treated by the present method can illustratively be a postmenopausal woman, for example of 50 years or older, or a man of 70 years or older.

In particular embodiments, the low bone density condition is associated with one or more of celiac disease, chronic liver disease, chronic pancreatitis, Cushing's syndrome, cystic fibrosis, estrogen deficiency, fat malabsorption syndromes, hyperparathyroidism, hyperthyroidism, inflammatory bowel disease, type 2 diabetes, or usage of a cyclosporin, heparin, histamine H2 receptor antagonist, parathyroid hormone, proton pump inhibitor, steroid or systemic retinoid drug.

A total daily dose of about 250 to about 1500 mg elemental calcium equivalent will generally be found useful according to the present therapeutic method. As in the use of the composition as a nutritional supplement, the total daily dose can be provided in one or more, for example 1 to 10, more typically 1 to 3, unit doses of a composition of the invention; where 2 or more doses are administered daily, they are preferably administered separately, at different times of the day. Again, it is desirable to administer the composition perorally, preferably at mealtimes.

Illustratively, a minimum total daily dose of about 300, about 350, about 400, about 450 or about 500 mg elemental calcium equivalent can be administered. Illustratively, a maximum daily dose of about 1400, about 1300, about 1200, about 1100 or about 1000 mg elemental calcium equivalent can be administered. In one embodiment, the total daily dose is about 400 to about 1200 mg elemental calcium equivalent.

Administration of a composition of the invention for treating a low bone density condition can be at the subject's own initiative or prescribed by a physician, and may be a component of a therapeutic regimen that includes other interventions such as medication and/or dietary changes.

The invention is further illustrated but not limited by the following Examples.

EXAMPLES

Example 1

Capsule Compositions

Compositions 1-1 to 1-6 are prepared as capsules having ingredients as shown in Table 1. The amounts of ingredients shown are for a unit dose, in a single capsule or divided between two capsules as indicated. DCM=dicalcium malate; TCP=tricalcium phosphate.

The ingredients are dry-blended and encapsulated by standard methods of pharmacy. Where phytase is included, temperature of the blend is maintained below 40° C. to avoid possible loss of enzyme potency.

TABLE 1

Capsule compositions 1-1 to 1-6

| Ingredient | Composition: 1-1 Weight (mg) | 1-2 | 1-3 | 1-4 | 1-5 | 1-6 |
|---|---|---|---|---|---|---|
| DCM granular (29% Ca) | 355 | 355 | 355 | 355 | 888 | 532 |
| TCP anhydrous (38% Ca, 20% P) | 407 | 407 | 407 | 407 | | 676 |
| monosodium phosphate (26% P) | | | | | | 300 |
| phytase, 4500 FTU/g | | 50 | 50 | 50 | 50 | 50 |
| ferrous asparto glycinate | | | 257.5 | 257.5 | | |
| succinic acid 98% | | | | 155 | | |
| malic acid 98% | | | | 155 | | |
| ascorbic acid 98% | | 357 | 205 | 155 | | |
| microcrystalline cellulose M102 | 22 | 399 | 293.5 | 33.5 | 17.5 | 10 |
| magnesium stearate | 16 | 32 | 32 | 32 | 19.5 | 32 |
| total | 800 | 1600 | 1600 | 1600 | 975 | 1600 |
| no. of size 00 capsules | 1 | 2 | 2 | 2 | 1 | 2 |
| wt. of ingredients per capsule | 800 | 800 | 800 | 800 | 975 | 800 |

Example 2

Tablet Compositions

Compositions 2-1 to 2-6 are prepared as tablets having ingredients as shown in Table 2. The amounts of ingredients shown are for a single tablet. DCM=dicalcium malate; TCP=tricalcium phosphate.

The ingredients are dry-blended or granulated and tableted by standard methods of pharmacy. Where phytase is included, tableting pressure and temperature are controlled to avoid excessive heating that can cause loss of enzyme potency. If desired, an overage (e.g., 20%) of phytase can be added to the tableting blend to compensate for any loss of potency during processing.

TABLE 2

Tablet compositions 2-1 to 2-6

| Ingredient | Composition: 2-1 Weight (mg) | 2-2 | 2-3 | 2-4 | 2-5 | 2-6 |
|---|---|---|---|---|---|---|
| DCM granular (29% Ca) | 355 | 355 | 355 | 355 | 888 | 532 |
| TCP anhydrous (38% Ca, 20% P) | 407 | 407 | 407 | 407 | | 676 |
| monosodium phosphate (26% P) | | | | | | 300 |
| phytase, 4500 FTU/g | | 50 | 50 | 50 | 50 | 50 |
| ferrous asparto glycinate | | | 257.5 | 257.5 | | |
| succinic acid 98% | | | | 155 | | |
| malic acid 98% | | | | 155 | | |
| ascorbic acid 98% | | 357 | 205 | 155 | | |
| micro crystalline cellulose M102 | 22 | 7 | 2.5 | 33.5 | 42 | 10 |
| magnesium stearate | 16 | 24 | 23 | 32 | 20 | 32 |
| total | 800 | 1200 | 1300 | 1600 | 1000 | 1600 |

Example 3

Capsule Composition

Composition 3 is prepared as capsules having ingredients as shown in Table 3. The amounts of ingredients shown are for a single capsule. The ingredients are dry-blended and encapsulated by standard methods of pharmacy. DCM=dicalcium malate; TCP=tricalcium phosphate.

TABLE 3

Capsule composition 3

| Ingredient | Weight (mg) |
| --- | --- |
| DCM granular (29% Ca) | 213.1 |
| TCP anhydrous (38% Ca, 20% P) | 311.7 |
| disodium phosphate anhydrous (22% P) | 71.9 |
| zinc bisglycinate chelate | 21.6 |
| cholecalciferol 100,000 IU/g | 6.4 |
| vitamin K2 (menaquinone-7) 95% | 0.1 |
| genistein 98% | 29.2 |
| microcrystaline cellulose M102 | 17.7 |
| magnesium stearate | 4.0 |
| silicon dioxide fumed | 2.5 |
| total | 678.2 |

The Ca:P molar ratio of Composition 3 is approximately 1.8:1, close to the 1.6:1 ratio used in bone remodeling.

Example 4

Powder Blend Composition

Composition 4 is a powder blend for reconstitution with water or various types of milk, to form a shake or shake-like composition. Table 4 lists ingredients for the powder blend. The protein is derived from a high concentration protein isolated soy formulation (SUPRO® 783 available from DuPont U.S.A.) and a moderate concentration protein isolated soy formulation (SUPRO® LF IP available from DuPont U.S.A.). The powder blend also contains vitamin D, phosphorus, magnesium and other minerals and vitamins which are taken into account for label claims. The powder blend has a Ca:P ratio of 1.6:1. The powder blend may additionally contain standard filler ingredients.

TABLE 4

Powder blend composition 4

| Ingredient | Label | Weight (mg) |
| --- | --- | --- |
| SUPRO ® PLUS 783 | 18.4 g | 20,000 |
| SUPRO ® LF IP | 1.6 g | 6,000 |
| DCM granular (29% Ca) | 500 mg | 1900 |
| TCP anhydrous (38% Ca, 20% P) | 250 mg | 723 |
| disodium phosphate anhydrous (22% P) | 360 mg | 1136 |
| zinc bisglycinate chelate | 15 mg | 75 |
| cholecalciferol 100,000 IU/g | 800 IU | 12.8 |
| vitamin K$_2$ (menaquinone-7) 95% | 180 ug | 0.2 |
| genistein 98% | 54 mg | 59.4 |
| DiMagnesium Malate | 270 mg | 1485 |
| Stevia - as needed | | |
| Flavorants - as needed | | |
| total | | 45,000 |

What is claimed is:

1. A single dosage form comprising
   (a) one to a plurality of physiologically acceptable calcium salts and/or chelates, at least about 5% of the molar amount of calcium in the composition being in the form of one or more organic acid salts and/or chelates of calcium, and
   (b) one or more phosphorus-containing component(s) that provide, in total, up to about 250 mg elemental phosphorus and one or more phosphorus-rescuing component(s), wherein each phosphorus-rescuing component is a phosphohydrolase, a phytase or any other component that can break down phytic acid or phytate to release phosphorus in the body, wherein the total molar amount of phosphorus delivered by such phosphorus-containing component(s) and rescued by such phosphorus-rescuing component(s) is calculated to be about 33% to about 300% of the molar amount of calcium in the single dosage form;
   wherein the molar ratio of calcium to phosphorus provides phosphorus-sparing calcium supplementation.

2. The single dosage form of claim 1, further comprising one or more additional nutritional ingredients independently selected from the group consisting of ascorbic acid and salts and esters thereof, vitamin D, and salts and chelates of mineral nutrients other than calcium.

3. The single dosage form of claim 1, further comprising at least one salt and/or chelate of a mineral nutrient other than calcium, selected from the group consisting of magnesium aspartate, magnesium creatine chelate, magnesium glycinate chelate, magnesium glycyl glutamine chelate, magnesium lysyl glycinate chelate, iron bisglycinate chelate, ferrous asparto glycinate chelate, zinc arginate chelate, zinc glycinate chelate, zinc histinate chelate, chromium nicotinate glycinate chelate, copper glycinate chelate, manganese glycinate chelate, molybdenum glycinate chelate, vanadium nicotinate glycinate chelate and combinations thereof.

4. The single dosage form of claim 1, comprising dicalcium malate (DCM) as an organic acid salt and/or chelate of calcium.

5. The single dosage form of claim 4, further comprising tricalcium phosphate (TCP).

6. The single dosage form of claim 5, in a form of a tablet or a capsule comprising DCM in an amount equivalent to about 40 to about 80 mg elemental calcium, TCP in an amount equivalent to about 75 to about 150 mg elemental calcium, and greater than zero to about 150 mg dibasic sodium phosphate.

7. The single dosage form of claim 6, wherein each tablet or capsule further comprises one or more of zinc glycinate chelate in an amount equivalent to about 2.5 to about 5 mg elemental zinc, cholecalciferol in an amount of about 250 to about 500 IU, vitamin K2 in an amount of about 60 to about 120 μg, and genistein in an amount of about 20 to about 40 mg.

8. The single dosage form of claim 1, comprising phytase as a phosphorus-rescuing component, in an amount of about 0.1 to about 10 FTU (phytase units).

9. A single dosage form comprising
   (a) one to a plurality of physiologically acceptable calcium salts and/or chelates independently selected from the group consisting of calcium carbonate, monocalcium phosphate (MCP), dicalcium phosphate (DCP), hydroxyapatite, calcium citrate tetrahydrate, calcium citrate malate (CCM), calcium formate, calcium gluconate, calcium glycerophosphate, calcium bisglycinate, calcium lactate, calcium levulinate, dicalcium malate (DCM), calcium succinate and calcium tartrate; and
   (b) one or more phosphorus-containing component(s) and one or more phosphorus-rescuing component(s), wherein each phosphorus-rescuing component is a phosphohydrolase, a phytase or any other component that can break down phytic acid or phytate to release phosphorus in the body, wherein the phosphorus-containing component(s) contain up to about 250 mg elemental phosphorus, and wherein the total molar amount of phosphorus delivered by such phosphorus-containing component(s) and rescued by such phosphorus-rescuing component(s) is calculated to be about 33% to about 300% of the molar amount of calcium in the single dosage form;

wherein the molar ratio of calcium to phosphorus provides phosphorus-sparing calcium supplementation.

10. A single dosage form comprising
(a) about 250 to about 800 mg in total of one or more physiologically acceptable calcium salts and/or chelates; and
(b) a phosphorus-containing component that is separate from or partly or wholly provided by said one or more physiologically acceptable calcium salts and/or chelates, wherein the phosphorus-containing component contains up to about 250 mg elemental phosphorus; and
(c) a phosphorus-rescuing component is a phosphohydrolase, a phytase or any other component that can break down phytic acid or phytate to release phosphorus in the body;

wherein the molar ratio of calcium to phosphorus delivered by each dosage form is about 1:3 to about 3:1; and the molar ratio of calcium to phosphorus provides phosphorus-sparing calcium supplementation.

11. A method for supplementing mineral nutrition in a human subject, comprising orally administering to the subject one to a plurality of the single dosage form of claim 1 daily.

12. The method of claim 11, wherein a total daily dose of about 100 to about 1500 mg elemental calcium equivalent is administered.

13. A method for treating, retarding or reversing the progress of a low bone density condition in a human subject in need thereof, comprising orally administering to the subject one to a plurality of unit doses of the single dosage form of claim 1 daily.

14. The method of claim 13, wherein the low bone density condition is manifested as osteomalacia, osteopenia or osteoporosis.

15. The method of claim 13, wherein a total daily dose of about 250 to about 1500 mg elemental calcium equivalent is administered.

16. The single dosage form of claim 1, wherein the phosphorus-containing component is separate from said one or more physiologically acceptable calcium salts and/or chelates.

17. The single dosage form of claim 1, wherein the phosphorus-containing component is partly provided by said one or more physiologically acceptable calcium salts and/or chelates.

18. The single dosage form of claim 9, wherein the phosphorus-containing component is separate said one or more physiologically acceptable calcium salts and/or chelates.

19. The single dosage form of claim 10, wherein the phosphorus-containing component is separate from said one or more physiologically acceptable calcium salts and/or chelates.

20. The single dosage form of claim 10, wherein the phosphorus-containing component is partly provided by said one or more physiologically acceptable calcium salts and/or chelates.

21. The single dosage form of claim 9, wherein the phosphorus-containing component is partly provided by said one or more physiologically acceptable calcium salts and/or chelates.

* * * * *